United States Patent
Suh et al.

(10) Patent No.: US 10,117,753 B2
(45) Date of Patent: Nov. 6, 2018

(54) STABILIZING VERTEBRAE WITH EXPANDABLE SPACERS

(71) Applicants: Sean Suh, Plymouth Meeting, PA (US); Chad Glerum, Pennsburg, PA (US); Damien O'Halloran, Conshohocken, PA (US)

(72) Inventors: Sean Suh, Plymouth Meeting, PA (US); Chad Glerum, Pennsburg, PA (US); Damien O'Halloran, Conshohocken, PA (US)

(73) Assignee: Globus Medical, Inc., Audubon, PA (US)

( * ) Notice: Subject to any disclaimer, the term of this patent is extended or adjusted under 35 U.S.C. 154(b) by 180 days.

(21) Appl. No.: 14/106,036

(22) Filed: Dec. 13, 2013

(65) Prior Publication Data

US 2014/0128978 A1  May 8, 2014

Related U.S. Application Data

(62) Division of application No. 13/303,527, filed on Nov. 23, 2011, now Pat. No. 8,632,593.

(51) Int. Cl.
*A61F 2/44* (2006.01)
*A61F 2/30* (2006.01)
(Continued)

(52) U.S. Cl.
CPC .......... *A61F 2/442* (2013.01); *A61F 2/30721* (2013.01); *A61F 2/441* (2013.01); *A61F 2002/2817* (2013.01); *A61F 2002/2835* (2013.01); *A61F 2002/304* (2013.01); *A61F 2002/30019* (2013.01); *A61F 2002/3052* (2013.01); *A61F 2002/30062* (2013.01); *A61F 2002/3093* (2013.01); *A61F 2002/30224* (2013.01); *A61F 2002/30367* (2013.01); *A61F 2002/30373* (2013.01); *A61F 2002/30401* (2013.01); *A61F 2002/30405* (2013.01); *A61F 2002/30462* (2013.01); *A61F 2002/30484* (2013.01); *A61F 2002/30504* (2013.01); *A61F 2002/30538* (2013.01);
(Continued)

(58) Field of Classification Search
CPC .... A61F 2/441; A61F 2002/443; A61F 2/442; A61F 2/4425; A61F 2/4611
See application file for complete search history.

(56) References Cited

U.S. PATENT DOCUMENTS 4,657,550 A * 4/1987 Daher ................. A61F 2/44
                                                        606/246
4,772,287 A    9/1988 Ray et al.
(Continued)

*Primary Examiner* — Julianna N Harvey

(57) ABSTRACT

A spinal distractor and stabilizer has resilient, conformable bone contacting sections which are separated by an expandable chamber that extends from one of the sections, and which forms a ratchet with the section, ensuring that once expanded by being filled with a substance, cannot contract absent intervention by a medical practitioner. The stabilizer may be filled with a material which solidifies, after which some or all of the device may biodegrade. The device may also be provided in separable portions to facilitate implantation. The conformable sections distribute the distraction and stabilizing force evenly over the bone surface, reducing the incidence of disruption to the integrity of the bone.

11 Claims, 4 Drawing Sheets

(51) Int. Cl.
　　　*A61F 2/48*　　　　(2006.01)
　　　*A61F 2/28*　　　　(2006.01)
(52) U.S. Cl.
　　　CPC ............... *A61F 2002/30556* (2013.01); *A61F 2002/30581* (2013.01); *A61F 2002/30583* (2013.01); *A61F 2002/30584* (2013.01); *A61F 2002/30601* (2013.01); *A61F 2002/30607* (2013.01); *A61F 2002/30616* (2013.01); *A61F 2002/30677* (2013.01); *A61F 2002/30754* (2013.01); *A61F 2002/30841* (2013.01); *A61F 2002/30995* (2013.01); *A61F 2002/448* (2013.01); *A61F 2002/4475* (2013.01); *A61F 2002/485* (2013.01); *A61F 2002/487* (2013.01)

(56) References Cited

U.S. PATENT DOCUMENTS

| | | | | |
|---|---|---|---|---|
| 5,236,460 | A * | 8/1993 | Barber | A61F 2/441 403/109.7 |
| 5,549,679 | A | 8/1996 | Kuslich | |
| 5,723,013 | A | 3/1998 | Jeanson et al. | |
| 6,176,881 | B1 | 1/2001 | Schar et al. | |
| 6,375,682 | B1 * | 4/2002 | Fleischmann | A61F 2/4425 623/17.12 |
| 6,648,917 | B2 | 11/2003 | Gerbec et al. | |
| 7,291,171 | B2 * | 11/2007 | Ferree | A61F 2/34 623/17.11 |
| 7,645,301 | B2 | 1/2010 | Hudgins et al. | |
| 7,824,445 | B2 | 11/2010 | Biro et al. | |
| 7,887,588 | B2 * | 2/2011 | Rapp | A61F 2/4455 623/17.11 |
| 8,123,810 | B2 * | 2/2012 | Gordon | A61B 17/7005 623/17.15 |
| 8,377,138 | B2 | 2/2013 | Reo et al. | |
| 8,388,685 | B2 | 3/2013 | Lombardo et al. | |
| 2003/0171813 | A1 * | 9/2003 | Kiester | A61F 2/447 623/17.11 |
| 2004/0133280 | A1 * | 7/2004 | Trieu | A61F 2/44 623/17.16 |
| 2004/0162618 | A1 | 8/2004 | Mujwid et al. | |
| 2005/0165485 | A1 * | 7/2005 | Trieu | A61F 2/4425 623/17.13 |
| 2005/0182416 | A1 * | 8/2005 | Lim | A61B 17/025 606/90 |
| 2005/0197702 | A1 | 9/2005 | Coppes et al. | |
| 2006/0030857 | A1 * | 2/2006 | de Villiers | A61F 2/4611 606/90 |
| 2006/0142861 | A1 * | 6/2006 | Murray | A61F 2/442 623/17.13 |
| 2006/0241770 | A1 * | 10/2006 | Rhoda | A61F 2/44 623/17.15 |
| 2007/0050032 | A1 * | 3/2007 | Gittings | A61F 2/442 623/17.12 |
| 2007/0270828 | A1 | 11/2007 | Bruneau et al. | |
| 2007/0270968 | A1 * | 11/2007 | Baynham | A61F 2/447 623/17.11 |
| 2008/0114367 | A1 * | 5/2008 | Meyer | A61B 17/025 606/90 |
| 2008/0288073 | A1 * | 11/2008 | Renganath | A61F 2/4455 623/17.12 |
| 2009/0240334 | A1 | 9/2009 | Richelsoph | |
| 2010/0106190 | A1 | 4/2010 | Linares | |
| 2010/0145456 | A1 | 6/2010 | Simpson et al. | |

\* cited by examiner

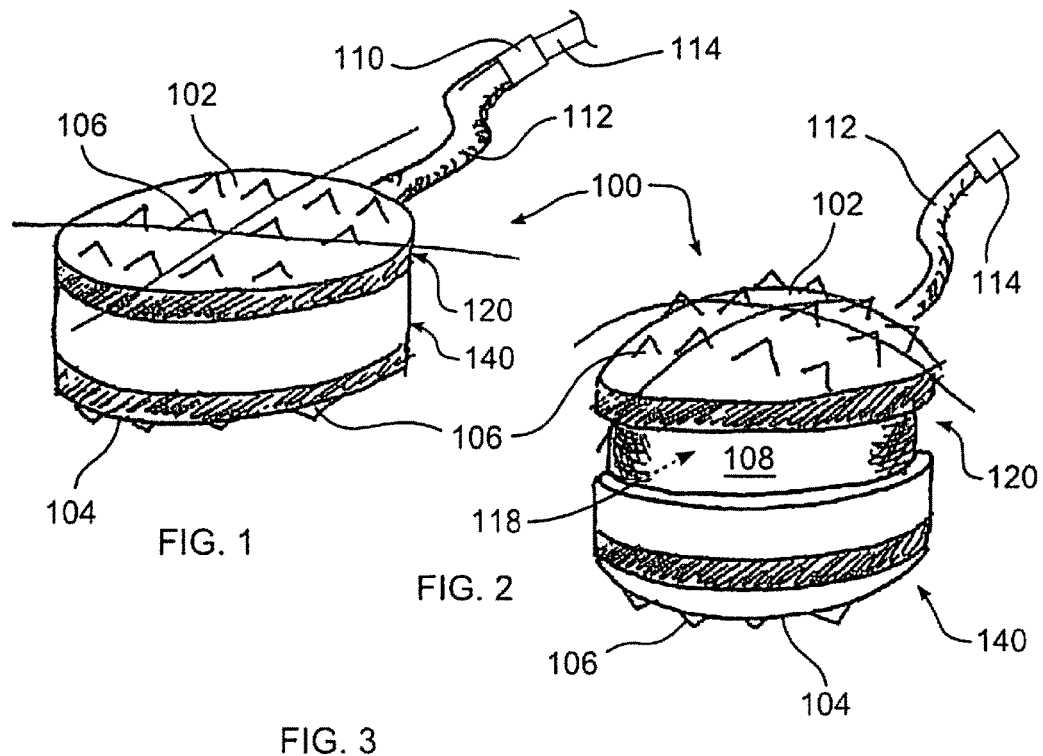
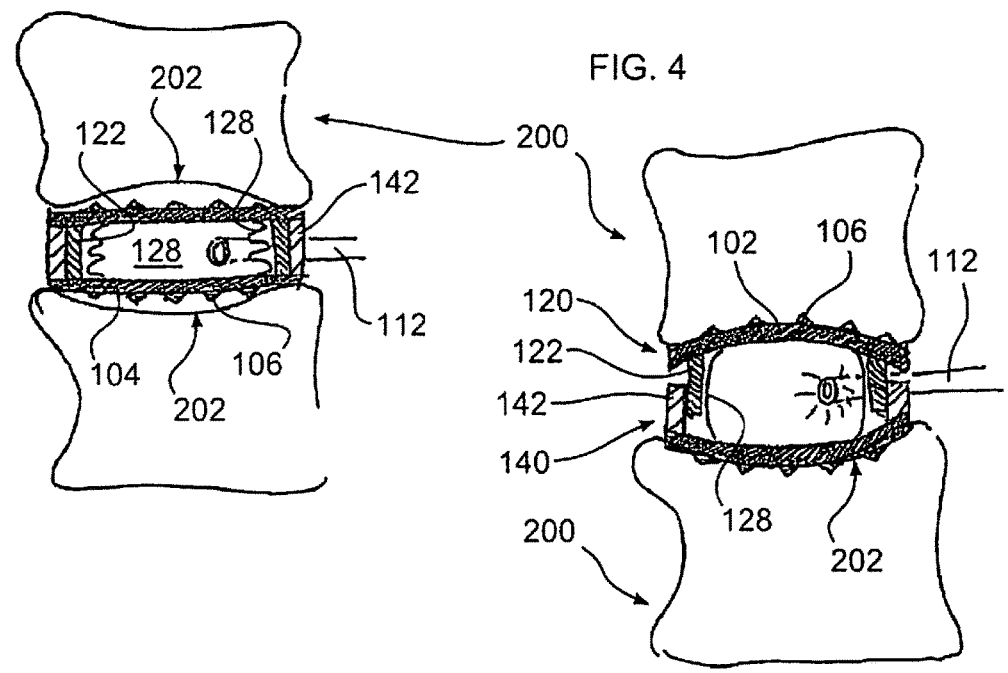

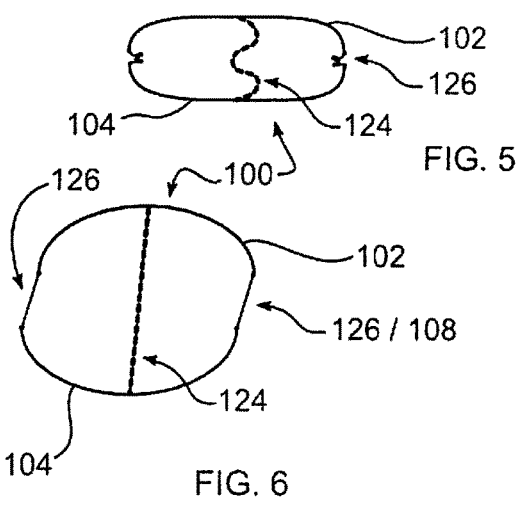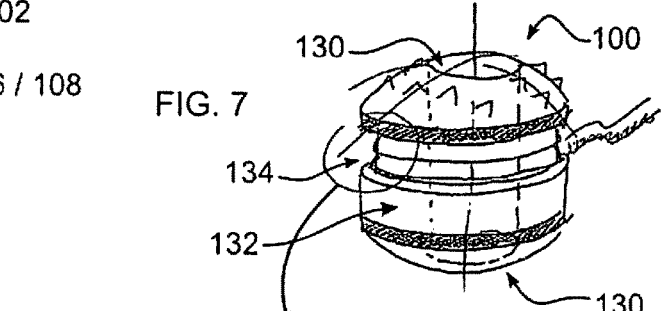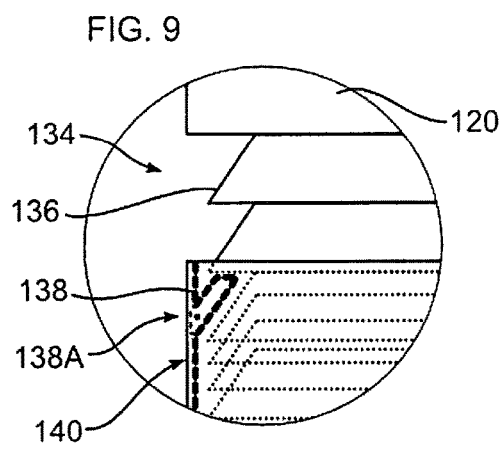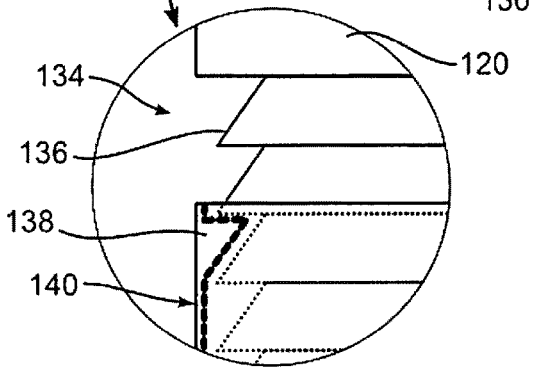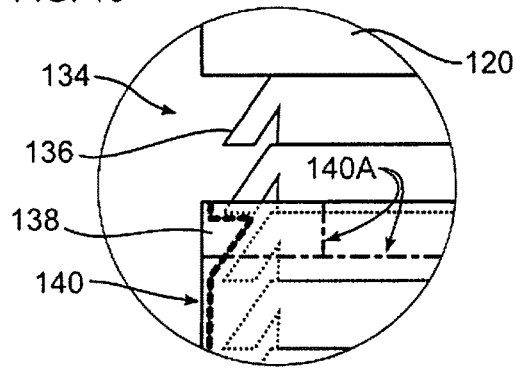

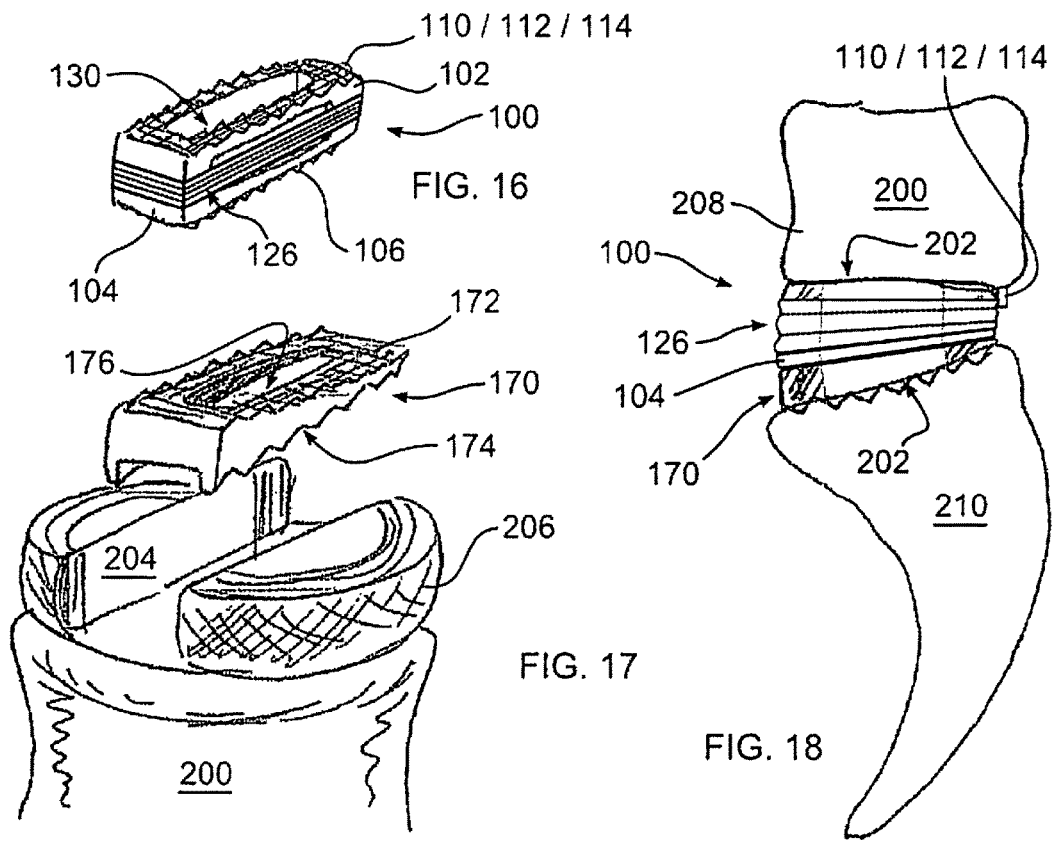
FIG. 16
FIG. 17
FIG. 18
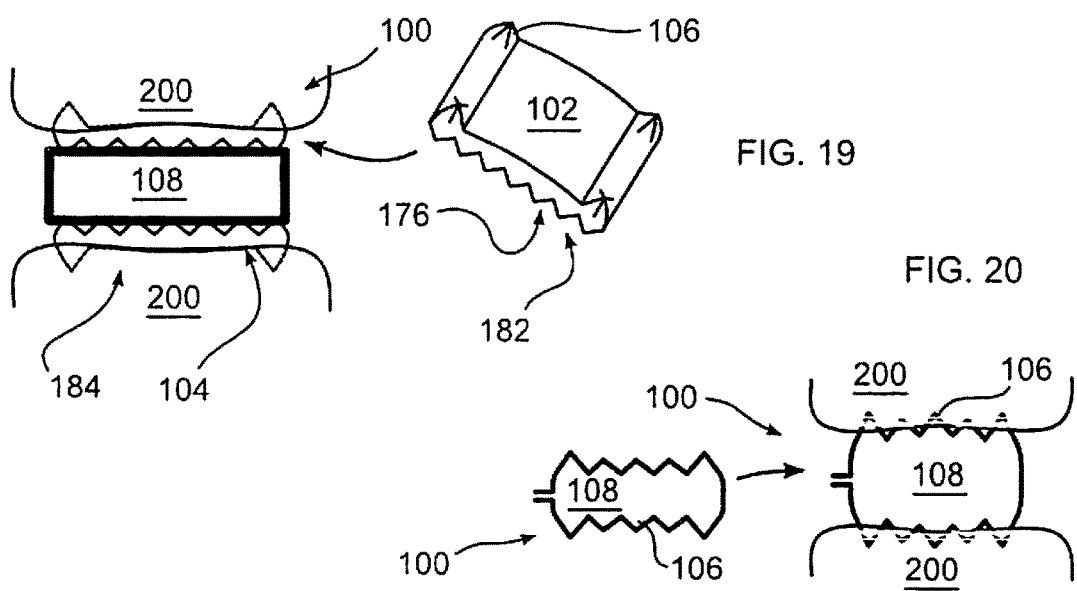
FIG. 19
FIG. 20

STABILIZING VERTEBRAE WITH EXPANDABLE SPACERS

CROSS-REFERENCE TO RELATED APPLICATIONS

The present application is a divisional of U.S. patent application Ser. No. 13/303,527, filed on Nov. 23, 2011, now U.S. Pat. No. 8,632,593. The previous application is incorporated by reference in its entirety.

FIELD OF THE INVENTION

The invention relates to systems and methods for stabilizing and restoring intervertebral spacing, and in particular, to expandable or inflatable intervertebral implants

BACKGROUND OF THE INVENTION

The vertebral or spinal column is a flexible assembly of vertebrae stacked on top of each other extending from the skull to the pelvic bone which acts to support the axial skeleton and to protect the spinal cord and nerves. The vertebrae are anatomically organized into four generalized body regions identified as cervical, thoracic, lumbar, and sacral; the cervical region including the top of the spine beginning in the skull, the thoracic region spanning the torso, the lumbar region spanning the second back, and the sacral region including the base of the spine ending with connection to the pelvic bone. With the exception of the first two cervical vertebrae, cushion-like intervertebral discs separate adjacent vertebrae.

The stability of the vertebral column during compression and movement is maintained by the intervertebral discs. Each disc includes a gel-like center surrounded by a fibrous ring. The gel-like center, or nucleus pulposus, provides strength and shock absorption, whereby the disc can absorb and distribute external loads. The nucleus pulposus contains a mixture of type II collagen dispersed in a proteoglycan matrix. The fibrous ring, or annulus fibrosus, provides stability during motion, and contains laminated rings of type-I collagen. Thus, the annulus fibrosis and the nucleus pulposus are interdependent, as the annulus fibrosis keeps the nucleus pulposus in place, and the nucleus pulposus aligns the annulus fibrosus to accept/distribute external loads. The integrity of the composition and structure of the intervertebral disc is necessary to maintain normal functioning of the intervertebral disc.

Many factors can adversely alter the composition and structure of the intevertebral disc, such as normal physiological aging, mechanical injury or trauma, or disease, resulting in impairment or loss of disc function. For example, the content of proteoglycan in the nucleus pulposus declines with age, thus, it follows that the ability of the nucleus pulposus to absorb water concurrently declines. Therefore, in normal aging the disc progressively dehydrates, resulting in a decrease in disc height and possible de-lamination of the annulus fibrosus. Mechanical injury can tear the annulus fibrosis allowing the gel-like material of the nucleus pulposus to extrude into the spinal canal and compress neural elements. Growth of a spinal tumor can impinge upon the vertebrae or disc, potentially compressing nerves. Regardless of the cause, many of these disc pathologies become severe enough to require surgical intervention.

In most cases, surgical intervention is a partial or complete removal of the damaged intervertebral disc material, and is termed a discectomy. While the discectomy may eliminate the problems associated with the damaged disc, it creates a void in the intervertebral space that, if left empty, can destabilize and possibly collapse the vertebrae, with adverse consequences. A device may be placed within the intervertebral space to increase stability, and to reduce the possibilities, for example, of disc collapse or the displacement of intervertebral tissue.

The art described in this section is not intended to constitute an admission that any patent, publication or other information referred to herein is "prior art" with respect to this invention, unless specifically designated as such.

SUMMARY OF THE INVENTION

In accordance with the disclosure, a joint distraction and stabilization device comprises a first bone contacting section having a first surface conformable to a surface of a first bone on one side of the joint; a second bone contacting section having a second surface conformable to a surface of a second bone on an opposite side of the joint; an expandable element positionable between the first and second bone contacting sections, the expandable element having an inlet port through which a filling medium may be passed into the expandable element under a filling pressure sufficient to expand and increase a dimension of the expandable element along an axis extending between the first bone and the second bone; at least one pawl extending from at least one of the first or second bone contacting sections; and at least one ratchet extending from the expandable element, the at least one ratchet passable past and engageable with the at least one pawl when the expandable element is expanded by pressure, and not passable past the at least one pawl when the at least one ratchet and at least one pawl are engaged and the filling pressure is reduced.

In various embodiments, at least one of the at least one pawl and at least one of the at least one ratchet are resiliently deflectable to be passable past the other; at least one of the at least one pawl and at least one of the at least one ratchet are hinged to be passable past the other; the inlet port includes a valve operative to maintain a pressure of the filling medium within the expandable element; the fillable medium increases in solidity after being passed into the expandable element; and a substantial portion of the device biodegrades after the fillable medium increases in solidity.

In yet further embodiments, the first and second bone contacting sections and the expandable element include mutually communicating apertures whereby a channel is formed extending from the first bone to the second bone; a material for promoting bone growth between the first and second bones is placed inside the aperture; the first bone contacting section includes a first side wall extending towards the second bone contacting section, and the second bone contacting section includes a second side wall extending towards the first bone contacting section, the first and second side walls telescoping in mutual relative conformity.

In another embodiment, the spacer further includes an extension extending from the inlet to a position away from bones of the joint; the extension is separable from the inlet; the spacer further includes projections extending from at least one of the first and second bone contacting sections to engage bone of the joint, thereby securing the at least one of the first and second bone contacting sections from lateral movement relative to an axis extending from the first bone to the second bone; at least one of the first or second bone contacting sections is separable from the expandable element.

In accordance with the disclosure, the bones may be of any joint in the body, the device advantageously utilized for example where the bones are vertebral bodies.

In further embodiments, the expandable element is formed of a resilient material; at least one of the first and second bone contacting sections resiliently conforms to a shape of the first or second bone, respectively; and the expandable element expands non-uniformly, thereby disposing the first and second bone contacting sections in substantially non-parallel conformity with respect to each other, when the first and second bone contacting sections are in contact with the first and second bones, respectively.

An a further embodiment of the disclosure, a joint distraction and stabilization device for the spine, comprises a first bone contacting section having a first resilient surface conforming to a surface of a first vertebral endplate of a first vertebra; a second bone contacting section having a second resilient surface conforming to a surface of a second vertebral endplate of an adjacent, second vertebra; an expandable element positioned between the first and second bone contacting sections, the expandable element having an inlet port through which a filling medium may be passed into the expandable element under a first pressure to expand and increase a height of the expandable element along an axis extending between the first bone and the second bone; at least one pawl extending from at least one of the first or second bone contacting sections; and at least one ratchet extending from the expandable element, the at least one ratchet passable past and engageable with the at least one pawl when the expandable element is expanded by pressure, and not passable past the at least one pawl when the at least one ratchet and at least one pawl are engaged and the filling medium is under a second, lower pressure, whereby a height of the device is substantially maintained. In an embodiment, the at least one pawl and the at least one ratchet are disengageable, whereby a height of the device may be reduced.

In accordance with a yet further embodiment, a joint distraction and stabilization device for the spine, comprises first and second vertebral endplate contacting sections having first and second resilient surfaces having projections, respectively; and an expandable element positioned between the first and second vertebral endplate contacting sections and extendable from at least one of the first and second vertebral endplates, the expandable element having an inlet port through which a filling medium may be passed into the expandable element under a first pressure to expand and increase a height of the expandable element along an axis extending between the first bone and the second bone to thereby distract the joint, the first pressure further operative to cause the first resilient surface to resiliently conform to a surface of a first vertebral endplate of a first vertebra, and to cause the second resilient surface to resiliently conform to a surface of a second vertebral endplate of an adjacent, second vertebra.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 1 depicts a spacer in accordance with the disclosure, in a non-expanded configuration;

FIG. 2 depicts the spacer of FIG. 1, expanded, illustrating convex bone engaging surfaces;

FIG. 3 depicts a cross-section through the spacer of FIG. 1, taken along an axis extending between bones of a joint, the spacer positioned between bones of the joint, illustrating telescoping side walls and an expandable interior reservoir or chamber, the spacer in a non-expanded configuration;

FIG. 4 depicts the spacer of FIG. 3, in an expanded configuration;

FIG. 5 depicts an alternative spacer in accordance with the disclosure, including resilient side walls, and a limiting tether, in an unexpanded configuration;

FIG. 6 depicts the spacer of FIG. 5, in an expanded configuration, a lateral displacement limited by the tether;

FIG. 7 depicts a further embodiment of the disclosure, including an expandable element having a through-hole for bone graft packing and a sidewall including ratchets;

FIG. 8 depicts a detailed area of the embodiment of FIG. 7, illustrating a cross section through the spacer of FIG. 7, taken along a vertical axis of the device, as illustrated, showing one embodiment ratchet and pawl configuration;

FIG. 9 depicts the detailed area of the embodiment of FIG. 7, illustrating an alternative embodiment including a hinged pawl, as well as nested ratchets;

FIG. 10 depicts the detailed area of the embodiment of FIG. 7, illustrating a resiliently deflectable ratchet, and a break-away portion of a spacer operative to disengage the ratchet and pawl;

FIGS. 16 and 17 depict an alternative embodiment of a spacer in accordance with the disclosure, including a body that is expandable in a non-linear manner, or that may be combined with a ramped spacer, to accommodate lordotic bone configurations;

FIG. 18 depicts the spacers of FIGS. 16 and 17 implanted between two bones;

FIG. 19 depicts a separable spacer portion combinable with an expanding element of the disclosure; and FIG. 20 depicts a resilient expanding chamber in accordance with the disclosure, including integral projections, in a deflated configuration, and inflated between two bones of the body.

DETAILED DESCRIPTION OF THE PREFERRED EMBODIMENTS

Figure 11:
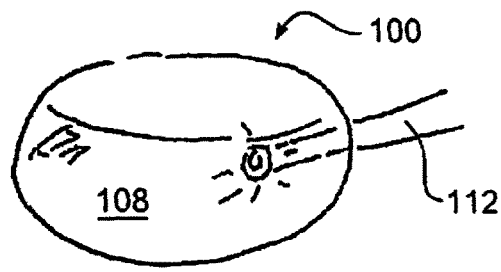
FIG. 11 depicts an alternative embodiment of the disclosure, including a resilient, inflatable spacer in an expanded configuration.

Detailed embodiments are disclosed herein; however, it is to be understood that the disclosed embodiments are merely examples and that the systems and methods described below can be embodied in various forms. Therefore, specific structural and functional details disclosed herein are not to be interpreted as limiting, but merely as a basis for the claims and as a representative basis for teaching one skilled in the art to variously employ the present subject matter in virtually any appropriately detailed structure and function. Further, the terms and phrases used herein are not intended to be limiting, but rather, to provide an understandable description of the concepts.

The terms "a" or "an", as used herein, are defined as one or more than one. The term plurality, as used herein, is defined as two or more than two. The term another, as used herein, is defined as at least a second or more. The terms "including" and "having," as used herein, are defined as comprising (i.e., open language). The term "coupled," as used herein, is defined as "connected," although not necessarily directly, and not necessarily mechanically.

In accordance with the disclosure, spinal disc spacers 100 are provided to stabilize and/or distract spinal joints, and are advantageously configured to be disposed between vertebral body end plates 202 of successive vertebrae 200. In an embodiment, spacers 100 conform to an exterior or interior configuration of the vertebral end plates 202. As such, a spacer 100 distributes body weight more effectively over a greater area of end plate 202, and thus prevents, reduces an incidence of, or lessens the severity of an end plate 202 failure in patients with weakened vertebral bodies. In an embodiment of the disclosure, portions of spacer 100 are formed with one or more rigid materials, such as metal or PEEK, and end plate contacting portions are advantageously formed with one or more relatively more flexible, conformable materials.

With reference to FIG. 1, an expandable spacer 100 includes first and second engagement surfaces 102, 104, each sized and dimensioned to engage a vertebral end plate 202 (FIG. 3). In accordance with an embodiment of the disclosure, one or both of surfaces 102 are advantageously provided with barbs, protrusions, or projections 106 shaped to securely engage body tissue at a surface of vertebral end plate 202. An expandable space, reservoir, chamber, or element 108 is positioned between surfaces 102, 104, and is operative to expand, pushing or telescoping surfaces 102, 104 apart, relative to each other. Expandable element 108 is advantageously expanded by absorbing fluid or other filling medium 118, or by being filled with a gas or liquid, in the manner of a balloon, thereby forming a greater internally contained volume, and a taller profile along a superior-anterior axis, or an axis defined to extend from one bone to another, when implanted between vertebrae.

In an embodiment, a connector 110 is advantageously provided upon a surface of expandable element 108, or at an end of an extending filler port 112, as shown in FIG. 1, and is operative to facilitate forming a connection to a filling channel 114 extendable outside a patient's body. The filling medium 118 is passed under pressure through filling channel 114 and port 112, to pass into expandable element 108. In another embodiment, connector 110 is configured as a one-way or adjustable valve, whereby after removal of filling channel 114 and associated filling apparatus (not shown), a filling medium 118 cannot escape from expandable element 108. In another embodiment, the filling medium 118 is a substance that solidifies after being passed into expandable element 108, and a valve at connector 110 is not needed.

The filling medium 118 may include a gas, for example oxygen, nitrogen, carbon dioxide, or other gas. The filling medium 118 may additionally or alternatively include a liquid, for example water, saline, oil, gel, or a pH buffered solution. Materials which harden after passing into expandable element 108 may include two part components, materials which harden when exposed to air or a gas, or materials which set over time, including PMMA (polymethyl methacrylate), one or two part urethanes, epoxies, foams, resins, hydrogels, or silicones. It is advantageous if the filling medium 118 is biocompatible, non-toxic, or otherwise not harmful to the body in the event it is accidentally or deliberately released from expandable element 108.

In FIG. 2, filling medium 118 has been passed into expandable element 108, and has caused surfaces 102, 104 to become convex with respect to an exterior of spacer 100. As may be seen in FIGS. 3 and 4, end plates 202 are concave, at least in part, with respect to an exterior of vertebral body 200. In another embodiment, surfaces 102, 104 are formed as convex or partially convex, without being under pressure from filling medium 118.

In the embodiment of FIGS. 1-4, a first mating section 120 includes a first guide surface 122, and a second mating section 140 includes a second guide surface 142. As spacer 100 is expanded by the introduction of filling medium 118, first and second mating sections 120, 140 move apart relative to each other along respective inferior/superior axes, and first and second guide surface 122, 142 may mutual engage to prevent substantial displacement of first and second mating sections 120, 140 in a direction transverse to the respective inferior/superior axes. In an embodiment, first mating section 120 and first guide surface 122 form, for example, a piston shaped object, and second mating section 140 and second guide surface 142 form a mating cylinder shaped object. As such, the piston shaped object is guided by first guide surface 122 as it telescopes within the cylinder shaped object as defined by second guide surface 142.

Other mutually sliding forms besides a piston and cylinder may be formed; for example first and second guide surfaces 122, 142 may have the form of separated mutually sliding walls. First and second guide surfaces may be rigid or resilient, thereby enabling either elevation only along a substantially superior-anterior axis, or additionally enabling a predetermined amount of flexion, abduction, and or rotation of bones of the joint.

First and second guide surfaces 122, 142 may form a seal to maintain filling medium 118 within spacer 100. Alternatively, as shown in FIGS. 3-4, a flexible reservoir 128 is disposed within an interior of spacer 100 in fluid communication with filler port 112, the flexible reservoir expanding to increase a height of spacer 100, and further forms a sealed space which is operative to contain filling medium 118, maintaining the seal within a desired range of pressures.

First and second engagement surfaces 102, 104 are advantageously resilient, in one embodiment, so that as pressure is applied to surfaces 102, 104 by passage of filling medium 118 into expandable element 108, surfaces 102, 104 may conform to the contour and surface shape of facing bones of the joint. In this manner, a support pressure by spacer 100 against the bones is evenly distributed, and high pressure points or areas upon the bones are avoided.

As may be seen in FIGS. 5-6, in an alternative embodiment, first and second mating sections are tethered together, for example by a cord or cable 124, and relative movement is inhibited at least to the extreme limit of motion defined by a length of cable 124, and the location of attachments of cable 124 to first and second mating sections 120, 140. In FIG. 5, at low pressure or in the absence of introduced filling medium 118, cable 124 and flexible sidewalls 126 are folded to enable a first, close spacing of engagement surfaces 102, 104. In FIG. 6, after filling medium has been introduced as described elsewhere herein, surfaces 102, 104 are pushed apart, a distance between surfaces 102 and 104 limited by a length of cable 124, and or an extended length of flexible sidewalls 126. In FIG. 6, it may be seen that surfaces 102, 104 are laterally displaced with respect to each other, and a longitudinal inferior/superior axis.

Referring now to FIGS. 7-8, spacer 100 is formed as described with respect to the embodiment of FIGS. 1-4, with distinctions as follows. In one embodiment, a central opening, aperture, bore or through-hole 130 is formed through the body of the spacer 100. In some embodiments, the through-hole 130 extends from an upper surface to a lower surface of the spacer 100. A therapeutic substance (not shown) may be inserted into through-hole 130 prior to implanting or expanding spacer 100, whereby the therapeutic substance is maintained in contact with end plate 202 of vertebral body 200. Therapeutic substance may include any substance which confers a beneficial result to the patient, including for example, bone morphogenic material; autograft, isograft, allograft, or xenograft material, artificial or natural scaffolding, lyophilized bone, freeze-dried bone allograft (FDBA), deminieralized freeze-dried bone allograft (DFDBA), hydroxylapatite, tricalcium phosphate, bioglass, calcium sulphate, antibiotics, hormones, or therapeutic drugs. In an embodiment, through-hole 130 passes completely through spacer 100, whereby a material placed within through-hole 130 may contact both endplates 202 of adjacent vertebrae 200. As such, bone growth between end plates 202 is enabled, whereby a natural fixation may be achieved, for example through osteoconduction, osteoinduction, osteopromotion, or osteogenesis. In this case, it is advantageous to form a scaffold of bone tissue, or a material which promotes bone ingrowth, such as a porous matrix.

In some embodiments, through-hole 130 is advantageously sealed with respect to an interior of spacer 100, for example using an additional flexible sidewall 126 forming through-hole 130, whereby filling medium 118 may be contained under pressure within a sealed interior space 132 residing between through-hole 130 and expanding sidewall 134.

FIG. 8 is an enlarged view of the detail area encircled in FIG. 7, illustrating an alternative embodiment for maintaining an increased spacer 100 height in accordance with the disclosure. Expanding sidewall 134 is formed with spaced ratchets 136 engageable with pawl 138 formed as one or more separate pawl sections, or may be formed as a continuous ledge extending along an inner perimeter of second mating section 140. In either embodiment, pawl 138 may be formed with a resilient material, and ratchets 136 may additionally or alternatively be resilient and may compress or deflect, whereby a ratchet may pass over a pawl, although the parts are in interference. Alternatively, ratchets 136 or pawl 138 may be hinged. In an embodiment, pawl 138 may be formed as a continuous extension of the material of second mating section 140, for example as a molded formation. In use, as first and second engagement surfaces 102, 104 are separated relative to each other, as described elsewhere herein, successive ratchets 136 engage pawl 138, thereby substantially preventing first and second engagement surfaces from returning to a position closer together to each other, whether or not pressure is maintained within expandable element 108. The number of ratchets 136 is selected to correspond to the granularity or precision with which a surgical practitioner may wish to adjust a height of spacer 100. For example, each ratchet 136 may be spaced 0.5 mm to 2.0 mm from the next, but the spacing may be substantially less than or greater than this range, for example 0.01 mm to 10 mm. In addition, a spacing between ratchets 136 need not be uniform, and may for example, be initially larger and progressively smaller. Further, ratchets 136 may be positioned upon an inner or outer surface of either first or second mating section 120, 140, with one or more pawls 138 being positioned on a corresponding surface of the other of first or second mating section 120, 140.

Herein, the terms ratchet and pawl are used interchangeably, as either or both of pawl 138 and ratchet 136 may be configured to move to be passable past the other, for example by hinging, resiliently deflecting, or resiliently compressing.

In FIG. 9, it may be seen that pawl 138 is provided with a hinge 138A about which pawl may rotate. A resilient member, such as a spring (not shown) may be positioned between pawl 138 and a portion of second mating section 140, to bias pawl 138 into engagement with ratchet 136. Alternatively or additionally, discrete sections of ratchet 136 may be hinged in a similar manner. FIG. 9 depicts a further embodiment, wherein ratchets 136 are nested one within the other, and expand and un-nest under pressure from said fillable material, to thereby expand a height of spacer 100.

In FIG. 10, ratchet 136 is illustrated to resiliently extend from expanding sidewall 134, whereby ratchet 136 may deflect to pass pawl 138, and resiliently return to a former position to engage pawl 138 once past. Pawl 136 may be formed in a similar manner.

FIG. 10 additionally depicts that pawl 138 may be removed from second mating section 140 by separating a portion of second mating section 140 containing pawl 138 at one or more scored or otherwise weakened parting lines 140A. In this manner, spacer 100 may be reduced in height by separating pawl 138 from spacer 100 and moving first and second mating sections closer together. In another embodiment, first or second mating section 120, 140, expanding sidewall 134, or other spacer 100 component, may be crushed, fractured, bent, or otherwise changed in shape or configuration, for example using weakened areas such as described for parting lines 140A, to facilitate removal of spacer 100.

It should be understood that throughout this specification, spacer 100 may be inserted with first mating section 120 in an inferior position with respect to the patient's body, relative to second mating section 140, or may be used in any orientation deemed therapeutically beneficial by the medical practitioner.

Figure 13:
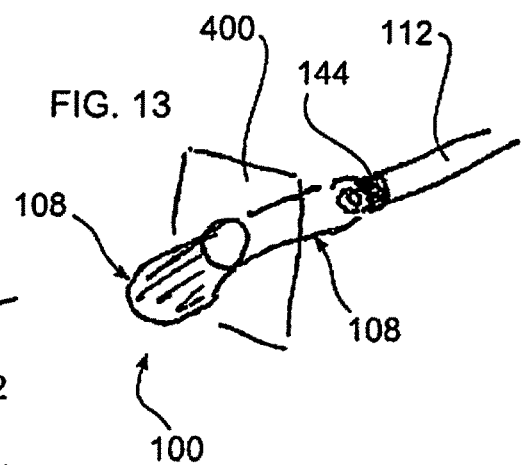
FIG. 13 depicts the spacer of FIG. 11, in a further deflated condition, the spacer being withdrawn from the body.
Figure 12:
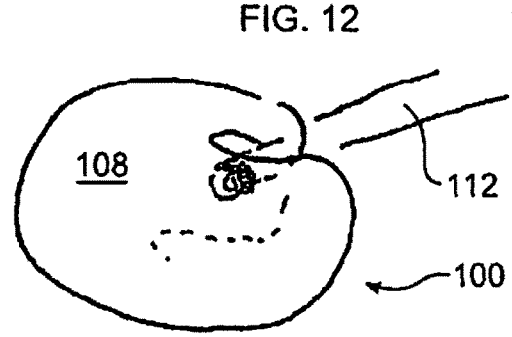
FIG. 12 depicts the spacer of FIG. 11, in a partially deflated condition.

Referring now to FIGS. 11-13, spacer 100 is diagrammatically illustrated in an expanded configuration. For clarity, although not illustrated in FIGS. 11-13, projections 106 and other elements of spacer 100 disclosed herein may advantageously be included in this and other embodiments. In one embodiment, spacer 100 is passed from outside the body into an interior of the body, such boundary symbolically represented as 400 in FIG. 13. Prior to implantation, a space may be formed between vertebral bodies, using methods known in the art. In an embodiment, a cannula, trocar, or other device operative to communicate exterior and interior portions of the body is positioned to extend into a target implantation space for spacer 100. Alternatively, a device may be used to form an aperture in the body, through which spacer 100 may be passed. Spacer 100 may then be pushed into the body, for example through a cannula, tube, device, or body opening, until it is positioned in a space between vertebral endplates.

In one embodiment, a portion of filler port 112 is passed into the body, and a remaining portion of spacer 100 is passed through filler port 112. For example, spacer 100 may be connected to filler port 112, deflated, and driven into a leading end 144 of filler port 112. Leading end 144 may be provided with a tissue piercing edge, whereby a separate trocar or cannula need not be used in order to pass filler port 112 into the body. Once leading end 144 is advantageously positioned within the body, filling medium 118 may be passed into filler port 112 to thereby drive spacer 100 out of filler port 112 and into the space to be expanded within the body, to thereafter increase in dimension as described elsewhere herein. Following distraction, stabilization, or other therapeutic procedure, spacer 100 may be deflated by withdrawing filling medium 118, after which spacer 100 may be removed in connection with filling port 112. In an alternative embodiment, filler port 112 may be removed after inflation of spacer 100, and removed from the body, leaving spacer 100 inflated. A valve 110 may be provided associated with spacer 100, whereby a separation of filler port 112, for example by unthreading a threaded connection, or breaking of a weakened portion, does not cause a deflation of spacer 100. In this manner spacer 100 may remain within the body for beneficial therapeutic purpose, for an extended time period, for example days, weeks, months, or years. In another embodiment, spacer 100 is passed into the body through a cannula or incision, and filler port 112 is thereafter connected for filling, and is subsequently left within the body, or is disconnected and removed from the body. In FIG. 12, spacer 100 is partially deflated. In FIG. 13, spacer 100 has been partly removed from the body, in this embodiment in connection with filler port 112 at leading end 144.

Figure 14:
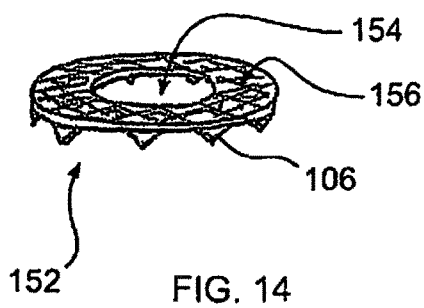
FIG. 14 depicts an artificial, modular endplate to be engaged with body tissue.
Figure 15:
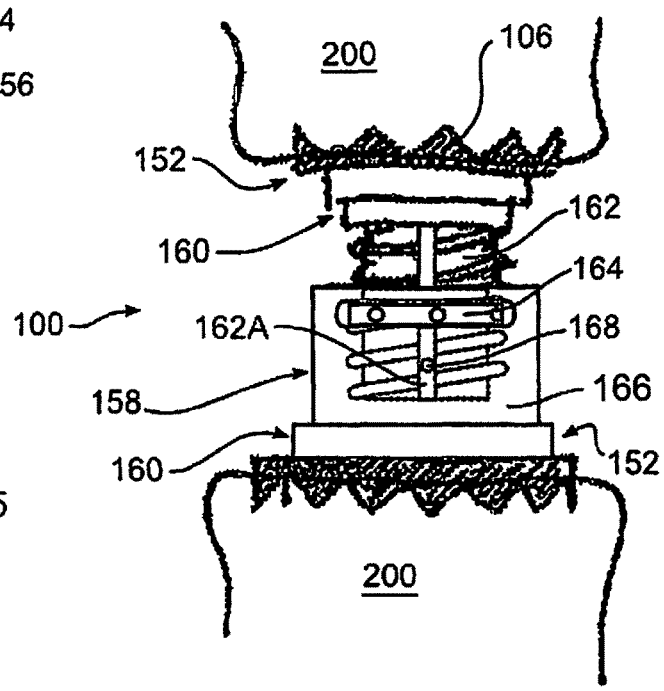
FIG. 15 depicts the end plate of FIG. 14, together with an alternative embodiment of a spacer body including a threaded expanding portion.

Referring now to FIGS. 14-15, the spacer system can include an artificial, modular end plate. The end plate can comprise an engagement platform 152 provided with one or more projections 106 operative to penetrate body tissue to securely maintain a position of engagement platform 152 with respect to the body. In some embodiments, platform 152 is shaped or curved to match an exterior surface of the bone with which it is to engage. For example, platform 152 may be convexly shaped to engage a vertebral end plate 202. An aperture 154 may be provided through the end plate to operatively enable bone growth therethrough, or to enable the passage of body tissue or other materials. A device contacting surface 156 may be provided with a knurled or roughened texture to promote secure engagement with a body 158 of spacer 100. Alternatively, device contacting surface 156 may be provided with a mechanical interlock, for example engaging digits, threaded apertures, or other interlock matable with a contacting surface 160 of spacer body 158. An alternative embodiment utilizing a portion analogous to platform 152 is discussed with respect to FIG. 19, below, and such description therein applies to platform 152, as well.

The modular end plate shown in FIG. 14 can work in conjunction with a spacer body. In some embodiments, the end plate can be attached to a first vertebral body. An expandable spacer body can then be inserted in between the first vertebral body and an adjacent second vertebral body. Upon expansion of the spacer body, the spacer body will press against the end plate, thereby pushing the end plate into the first vertebral body and provide a reinforced spacer system.

In the embodiment of FIG. 15, an alternative means of expanding spacer 100 is illustrated. More particularly, a threaded shaft 162 passes through a nut 164 rotatably disposed in attachment to a housing 166. Shaft 162 is prevented from rotating, whereby turning nut 164 causes shaft 162 to extend or retract from housing 166, to thereby expand or contract a height of spacer 100. Nut 164 may be rotatably connected to housing 166, and shaft 162 prevented from rotating, by any known means in the art. In one embodiment, an alignment projection 168 connected to housing 166 may extend into a slot 162A within shaft 162.

Engagement platform 152 may be combined with any other spacer 100 embodiment of this disclosure, enabling the selection of an engagement platform 152 best suited to the physiology and pathology of the patient, and the goals of the medical practitioner.

With reference to FIGS. 16-18, a spacer 100 is sized and shaped to be inserted within a space formed by removal of a portion of the nucleus pulposus 204 and possibly a portion of the disc annulus 206. In the illustrated application, spacer 100 is combined with a ramped, angular spacer 170 having non-parallel opposing external faces 172, 174. In some embodiments, either one or both of the spacer 100 or the angular spacer 170 are expandable. In this manner, a spacer 100 having substantially parallel faces may be used in locations where adjacent bony endplates are substantially non-coplanar relative to each other, as is the case with L5 (208) and the sacrum 210. Alternatively, either or both of spacer 100 and an angular spacer 170 may compensate for an angular displacement between adjacent bony surfaces. As may be seen in FIG. 18, flexible sidewalls 126 extend to differing amounts on opposing sides of spacer 100, while angular spacer 170 compensates for part of the angular differential between bony end plates 202.

Referring now to FIG. 19, spacer 100 is advantageously formed of separable portions 182, 184 wherein expandable element 108 is not fastened to one or both of engagement surfaces 102, 104, prior to implantation in a patient. In this manner, access to endplate 202 is improved. Where a fastener is passed through engagement surface 102, 104, access to a device contacting face 176 is unobstructed, facilitating passage and connection of the fastener. Alternatively, where it is desired to drive projections 106 into bone or body tissue, force may be applied to non-contacting face 186 without obstruction by additional elements of spacer 100, including for example expandable element 108 or the other of engagement surface 102, 104. Further, such other elements of spacer 100 may be protected during application of force, and installed after a separable portion is implanted and fastened to the body. In addition, once separable portions 182, 184 are secured to body tissue, they form a reliable and predictable platform or scaffold for other elements of spacer 100, and or for other implants. While four projections 106 are shown in FIG. 19, any number of projections 106 may be provided, depending on the type of body tissue to which projections 106 must be connected, as well as the forces expected to be applied to spacer 100, and the therapeutic goals of the practitioner.

Portions 182, 184 may be analogous to platform 152, described above with respect to FIG. 14, and such description may be applied to portions 182, 184, as well. For example, device contacting faces 176 may advantageously engage expandable element 108, or body 158 of spacer 100, as described for device contacting surface 156.

In FIG. 20, expandable element 108 contains integrally formed projections 106, and is a unitary structure that may be expanded with filling medium 118 to expand and drive projections 106 into body tissue. Alternatively, projections 106 may be absent, wherein expandable element 108 is maintained in place by bodily structures, or other implanted structures. The advantage of this expandable element 108 is that the expandable element itself serves as the entire implant. In some embodiments, to maintain the proper shape of the expandable element 108 in an intervertebral space, the expandable element 108 can be formed of cold molding. Alternatively, the wall thickness of the expandable element 108 can be controlled to maintain a desirable shape of the implant.

It should be understood that within this disclosure, projections 106 may extend from material from which they project, formed, for example, by molding. Alternatively, projections 106 may represent fasteners that are passed through one or more portions of spacer 100, and may include for example bone screws, barbed fasteners, staples, sutures, k-wires, polymeric anchors, or expanding anchors. Spacer 100 or any component of spacer 100 as described herein may alternatively be connected or secured within the body by adhesives or cements, for example including polymethyl-methacrylate (PMMA), methyl-methacrylate monomer (MMA), or acrylate-based plastics, although other forms of adhesives used in the body are known in the art.

In accordance with the disclosure, spacer 100 may be used to facilitate or promote inter-body fusion (IBF), and may provide stabilization and or distraction while reducing stress points upon bony structures, and in particular, fragile vertebral end plates. In addition, spacer 100 may be used alone or in combination with other spacers to create or restore healthy orientation of curvature of the spine or other jointed bones, for example to correct for extreme lordosis.

Spacers 100 may be formed to closely conform to patient physiology, for example by being shaped based upon imaging of a patient prior to manufacture and or implantation. Spacers 100 of the disclosure may be implanted using any known or hereinafter developed surgical implantation techniques, including minimally invasive, cannula based, mini-invasive, or fully open access, as well as anterior, posterior, anterio-lateral, or posterior-lateral approaches.

While a positioning of spacer 100 between adjacent vertebrae is illustrated and described herein, it should be understood that spacer 100 may be inserted into an interior of a vertebral body 200, to provide support from within the vertebrae. In this application, first and second engagement surfaces 102, 104 may advantageously be concave, to better conform to an interior configuration of the vertebral endplates 202. One or more vertebrae of a patent may be supported in this manner. Further, where spacer 100 is positioned between adjacent vertebrae, more than one spacer 100 may be used between adjacent vertebrae, and spacer 100 may be positioned at multiple levels, between different adjacent vertebrae.

Moreover, in addition or in alternative to the spine, spacer 100 may be positioned within other joint spaces of the body, for example in joints of the fingers, hand, wrist, elbow, shoulder, hip, knee, ankle, foot, and toes, to effectuate therapeutic distraction or stabilization of such joints. Spacer 100 is thus sized and shaped to correspond to the joint in which spacer 100 will be implanted, whether temporarily, or for a prolonged post-surgical period.

Any or all of spacer 100 may be formed using biodegradable materials whose use is understood within the art, whereby after stabilization has been achieved, spacer 100 may dissolve or otherwise deconstitute, advantageously without leaving potentially harmful material within the body. This may be advantageous, for example, where bone formation has fused adjacent vertebrae, and spacer 100 is no longer needed in order to foster stabilization. Alternatively, spacer 100 may be used in combination with other stabilization or therapeutic devices, and may only be needed for an initial period, during which, for example, healing of the body, curing of an additional device, or bio-integration of another device takes place, after which spacer 100 may advantageously biodegrade.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention.

All references cited herein are expressly incorporated by reference in their entirety. In addition, unless mention was made above to the contrary, it should be noted that all of the accompanying drawings are not to scale. There are many different features to the present invention and it is contemplated that these features may be used together or separately. Thus, the invention should not be limited to any particular combination of features or to a particular application of the invention. Further, it should be understood that variations and modifications within the spirit and scope of the invention might occur to those skilled in the art to which the invention pertains. Accordingly, all expedient modifications readily attainable by one versed in the art from the disclosure set forth herein that are within the scope and spirit of the present invention are to be included as further embodiments of the present invention.

What is claimed is:

1. A method of installing a spinal device in an intervertebral space, comprising:
   introducing a first bone contacting endplate having a first surface for contacting a surface of a first bone and a second surface into the intervertebral space;
   introducing a second bone contacting endplate having a third surface contacting a surface of a second bone and a fourth surface into the intervertebral space; and
   introducing an expandable element having an upper end and a lower end into the intervertebral space after introducing the first bone contacting endplate and the second bone contacting endplate such that the expandable element is positionable between said first and second bone contacting endplates,
   expanding the expandable element such that the upper end of the expandable element engages with the second surface of the first bone contacting endplate pushing the first bone contacting endplate against the first bone and the lower end of the expandable element engages with the fourth surface of the second bone contacting endplate pushing the second bone contacting endplate against the second bone,
   wherein the expandable element comprises a housing and a threaded shaft that passes through a nut and into the housing, wherein the threaded shaft is non-rotatable,
   wherein the expandable element remains in the intervertebral space.

2. The method of claim 1, wherein after expansion, the expandable element is attached to the first and second bone contacting endplates through mechanical interlocks.

3. The method of claim 1, wherein the expandable element engages the first and second bone contacting endplates after expansion of the expandable element.

4. The method of claim 1, wherein the upper end of the expandable element includes an upper surface and the lower end of the expandable element includes a lower surface and wherein at least a portion of the upper surface is angled with respect to at least a portion of the lower surface.

5. The method of claim 1, wherein the first and second bone contacting endplates include one or more projections for engaging the first and second bones.

6. The method of claim 1, wherein said bones are vertebral bodies.

7. The method of claim 1, wherein the nut is rotatably connected to the housing.

8. The method of claim 7, wherein the threaded shaft extends along a longitudinal length from a first end to a second end positioned within the housing, the threaded shaft comprises a slot that extends along the longitudinal length.

9. The method of claim 8, wherein the expandable element further comprises an alignment projection connected to the housing that extends into the slot.

10. The method of claim 1, further comprising turning the nut to cause the threaded shaft to extend from the housing to thereby expand a height of the spinal device.

11. The method of claim 1, further comprising turning the nut to cause the threaded shaft to retract into the housing to thereby contract a height of the spinal device.

\* \* \* \* \*